Sept. 8, 1964 H. KRAVITZ ETAL Re. 25,637

MEANS FOR VACCINATING

Original Filed Dec. 20, 1952

Inventors
Harvey Kravitz
Norman Zeltvin
by Bair, Freeman & Molinare
Attys.

United States Patent Office

Re. 25,637
Reissued Sept. 8, 1964

25,637
MEANS FOR VACCINATING

Harvey Kravitz, 9243 Avers Ave., Skokie, Ill., and Norman Lettvin, 527 W. Roscoe St., Chicago, Ill.

Original No. 2,817,336, dated Dec. 24, 1957, Ser. No. 327,136, Dec. 20, 1952. Application for reissue Dec. 21, 1959, Ser. No. 861,166
17 Claims. (Cl. 128—253)

Matter enclosed in heavy brackets [ ] appears in the original patent but forms no part of this reissue specification; matter printed in italics indicates the additions made by reissue.

This invention relates to a device for vaccinating people and more particularly to a device for standardizing vaccinations.

In present vaccination techniques, an amount of vaccine is deposited onto the skin of the individual and then the portion of the skin to which the vaccine is applied is scarified by using a sharp needle and repeatedly jabbing the needle into the area of the skin upon which the vaccine lies. The physician doing the vaccinating usually doesn't want to scarify too deeply as this may be rather painful, and at the same time if the scarification is insufficient, the vaccination does not "take." Therefore, the physician usually jabs the scarifying needle into the skin a few times hoping that at least one jab will take. Unfortunately, if they all take, the resulting scar may be large and unattractive. Also each physician may vary the number and size of scarifications, and as a consequence vaccinations vary in size and shape.

There is another problem present in present vaccination techniques which arises particularly in vaccinating children. The child is usually frightened and after the first jab from the needle jerks his arm or squirms, or anticipates the second jab and moves his body. In any event, movement of the child while the physician is scarifying may result in long scarifying scratches or in scarifications spaced far from each other—and the result is that there may be formed an excessively long or unattractive scar.

Regardless of the above problems of scarification it is also highly desirable to have resulting from the vaccination as uniform and small a scar as possible for obvious cosmetic reasons.

Thus, it is one object of this invention to provide a device for standardizing vaccinations by providing for no more than a predetermined number of scarifications within a limited area, or by scarifying over only a predetermined limited area, and with a predetermined pattern if desired.

Another object of this invention is to provide a scarification device for use in the vaccination process which is adapted to be mounted so as to restrict lateral movement thereof with respect to the area of the skin being scarified, whereby the possibility of enlarged vaccination scars is substantially eliminated.

A further object of this invention is to provide a device for accomplishing the objects set forth above, and which device is characterized by its simplicity of construction and of operation thereof, and by its relative inexpensiveness.

In our copending application Serial No. 320,724, filed November 15, 1952, *now issued as Patent No. 2,876,774 dated March 10, 1959,* we have described a novel method and apparatus for vaccinating. The general concept involved in that application related to the dispensing of vaccine and scarifying with the same instrumentality.

In view of the benefits derived as disclosed in said copending application, by dispensing vaccine and scarifying with the same instrumentality, it would be desirable to provide a device which accomplishes the objects set forth above as part of the combination of a vaccinating device which is used both for dispensing vaccine and for scarifying—and so, that is still another object of this invention. Thus, it is also an object of this invention to provide a new vaccinating instrumentality.

A further problem arises in that medical requirements are such that the vaccine dispensing means and scarifying means must be maintained sterile until use thereof is required, and, thus, still a further object of this invention is to provide a scarifying device, or a combination vaccine-dispensing and scarifying device which may easily be maintained sterile as by individual packaging in sterile packages, and which devices are to be discarded after a single use thereof.

Further objects and advantages of this invention will become apparent as the following description proceeds and the features of novelty which characterize this invention will be pointed out with particularity in the claims annexed to and forming part of this specification.

A preferred embodiment of the invention is shown in the accompanying drawing, in which.

Figure 1:
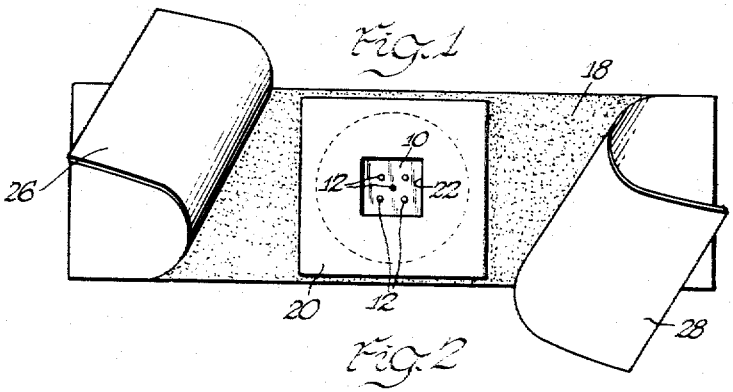
FIGURE 1 is a plan view of the novel scarifying device for standardizing vaccinations.
Figure 2:
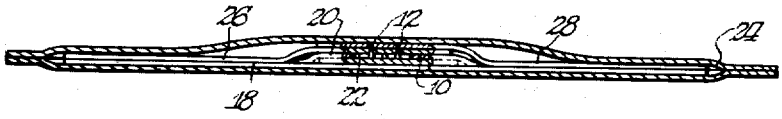
FIGURE 2 is a longitudinal cross-section view of the device in FIGURE 1 showing it packaged in a typical manner for distribution.
Figure 3:
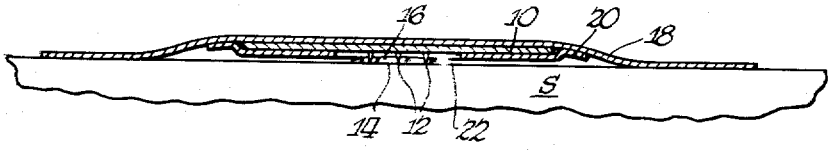
FIGURE 3 is an enlarged longitudinal cross-section view of the device of FIGURE 1 showing how it is positioned for use in scarifying the area of the skin to which the vaccine has been applied.

Referring now to the drawings, reference is had to the form of the device shown in FIGURES 1 to 3, particularly to FIGURE 3, wherein the device is shown in operation. There is shown a rigid plate member 10 having extending from a central portion thereof a predetermined plurality of scarifying points or needles 12 which are adapted to overlie an area 14 of the skin S to which the vaccine 16 has been applied. Means are provided to laterally position the member 10 so as to substantially eliminate possible lateral movement between the needles 12 and the skin area 14 while still affording movement of the needles 12 toward and away from the skin.

The means for accomplishing this lateral positioning of member 10 comprises a strip 18 of fabric or the like, to which said plate 10 is secured intermediate the ends of strip 18 by means of a cover patch 20. The strip 18 has adhesive on one side thereof adapted to secure said strip 18 to areas of the skin adjacent the skin area 14 which is to be [sacrified] *scarified.*

The fabric strip 18 is relatively inelastic, and, when once adhered to the skin, substantially fixes the position of the scarifying means relative to skin area 14, and restricts any lateral movement of the scarifying means 12 with respect to skin area 14. At the same time said fabric strip 18 affords sufficient movement of the needles 12 toward and away from skin area 14 to bring about scarification.

The rigid plate member 10 is secured in position on strip 18 by means of the cover patch 20. The patch 20 may be secured to strip 18 by any appropriate means, including the adhesive, which is already on the side of strip 18 to which the patch 20 is secured. Patch 20 has an aperture 22 therein through which extends the scarifying means 12.

The entire device shown in FIGURE 3 should be sterilized, by autoclaving or the like, and may be packaged individually in a sterile paper package 24, such as is commonly used in the packaging of individual bandages. Such an individual, sterile package 24 is shown in FIGURE 2. The strip 18 also may have sterile gauze members 26 and 28 secured to the adhesive portions thereof, in a manner well known and presently used in packaging of certain types of commercial adhesive bandages. The gauze strips overlie the plate member 10 and the scarifying needles 12 and maintain them free from contaminants. The layers of gauze 26 and 28 which overlie the scarifying means 12 are sufficient to prevent the scarifying means from piercing the paper package 24..

The scarifying needles 12 are made long enough to afford good scarifying therewith and short enough to prevent laceration even if buried in the skin to their full length. The plate member 10 is large enough to be engaged by at least the entire pressing area of a thumb or finger of a person manipulating the scarifying means. This permits the physician to apply sufficient pressure on the back of the plate member 10 to achieve scarification without any resultant discomfort to him, as might be occasioned if the plate member 10 were of smaller area. The member 10 also is adapted to engage a sufficient portion of the area of skin surrounding the area 14 being scarified and bear thereagainst to prevent unusual penetration of the needles 12 into the skin.

Figure 5:
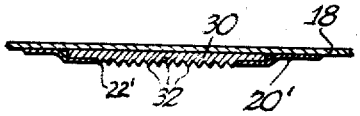
FIGURE 5 is a view taken on line 5—5 of FIGURE 4.
Figure 4:
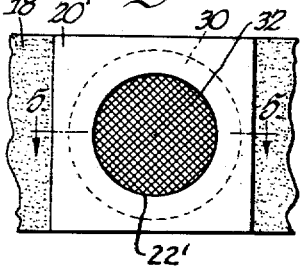
FIGURE 4 is a plan view of a modified form of scarifying device shown in FIGURES 1 to 3.

A modified form of the scarifying means shown in FIGURES 1 to 3 is shown in FIGURES 4 and 5 and includes a rigid plate 30 having serrations 32 in the outer surface thereof. Any member or patch having an abrasive surface, such as sandpaper or fabric having abrasive thereon, may be used as the scarifying means. The plate 30 is retained in position on fabric strip 18 by means of patch 20' which has an aperture 22' therein through which extends the scarifying means 32. The size and shape of aperture 22' determines and limits the area of skin which is being scarified, and thus the size of vaccinations may be standardized either by use of a predetermined number of needles 12, as shown in FIGURES 1 to 3, or by scarifying a predetermined area as limited by apertures 22' in FIGURES 4 and 5. Furthermore, the needles 12 may be arranged in a predetermined pattern, if desired, as may also be the shape of aperture 22'.

Figure 6:
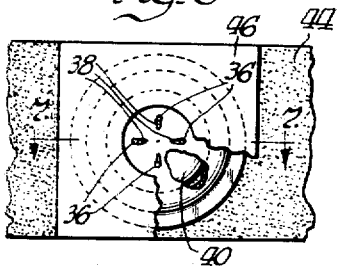
FIGURE 6 is a plan view of a modified form of the device which may be used both for dispensing the vaccine and for scarifying the skin area upon which the vaccine is dispensed.
Figure 7:
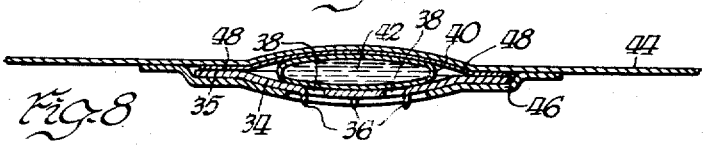
FIGURE 7 is an enlarged cross-section view taken on line 7—7 of FIGURE 6.

In the modified form shown in FIGURES 6 and 7, the scarifying member is shown in combination with means for dispensing the vaccine either prior to, or simultaneously with, the use of the scarifying member on the portion of the skin to which the vaccine is to be applied. Thus, in this form, the invention is a device for vaccinating people.

In this form of the invention, there is a dished rigid plate member 34, having a flange 35 for reasons hereinafter described, and having a predetermined number of scarifying members 36 projecting from the convex surface thereof, which scarifying members 36 are formed by piercing the dished rigid plate member 34 and bending the scarifying member 36 away from the surface of the dished rigid plate member 34. The forming of the scarifying members 36 by bending them away from the plate leaves a plurality of apertures 38 in plate 34 adjacent the scarifying members 36. Vaccine may be dispensed through the apertures 38 and may run down the scarifying members 36 adjacent the apertures 38 to be dispensed onto the skin. The size of the dispensing apertures 38 may be liimted to provide control of the flow of vaccine therethrough as taught in the above referred to copending application.

Positioned in the concave portion of the dished rigid plate member 34 is a frangible or puncturable capsule 40 containing liquid vaccine 42 therein. The dished rigid plate member 34 and capsule 40 are positioned on an adhesive fabric 44 with the capsule positioned between the dished rigid plate member 34 and the fabric strip 44. By pressing on the capsule 40 through the fabric strip 44, the capsule may be ruptured or broken, and the vaccine that is released may then be forced through apertures 38 in dished rigid plate member 34 onto the skin of the person being vaccinated. Thereafter, additional force applied to dished rigid plate member 34 will bring about scarification of the area of the skin to which the vaccine is applied. The dished rigid plate member 34 is maintained in position by a cover patch 46 in a manner similar to that shown in FIGURES 1 to 3.

In the use of the device shown in FIGURES 6 and 7, the adhesive strip 44 may first be adhered to the skin, and then, by pressure applied through adhesive strip 44 against capsule 40, the vaccine is released and dispensed through apertures 38 onto the skin, and continued pressure applied to dished rigid plate 34 brings about scarification by scarifying members 36.

A preferred method of use of this device comprises the rupturing of the capsule 40 prior to applying the device to the skin. After the capsule 40 has been ruptured and the vaccine 42 has been released, the vaccine 42 may be dispensed carefully, by controlled digital pressure, through the apertures 38 onto the skin. Such controlled dispensing is desirable so that only a desired amount of vaccine is dispensed. The apertures 38 are small enough so that the vaccine 42 does not flow readily therethrough and the vaccine 42 will be dispensed only under positive digital pressures.

Since the needles or scarifying members 36 are adjacent the apertures 38, the vaccine may feed down along said needles 36 and be dispensed therefrom without touching the needles 36 to the skin of the person. After the desired amount of vaccine has been dispensed, the adhesive strip 44 may be secured to the skin with the scarifying member 36 positioned above the vaccine which has been dispensed onto the skin. Then by applying pressure to the dished rigid plate member 34 the scarifying members 36 are caused to scarify the skin. This pressure may be applied to the flange 35 of dished rigid plate 34 and in this way no additional pressure is applied to the capsule 40 and vaccine 42, and no additional vaccine will be dispensed during the scarifying operation.

The fabric strip 44 is sufficiently fluid resistant to delay leakage of vaccine 42 therethrough after the capsule 40 has been ruptured and while the vaccine 42 is being dispensed through apertures 38. There may also be included an extra sterile flap 48 of close-mesh fabric, rubber, or the like, positioned between the dished rigid plate member 34 and the fabric strip 44. The purpose of the flap 48 is to provide resistance to leakage or permeation of the vaccine 42 therethrough, and through the fabric strip 44. In addition, the flap 48 may be secured directly to the flange 35 of the dished rigid plate member 34 by any appropriate means, and in a fluid-tight seal, if desired. The dished rigid plate member 34, capsule 40 and flap 48 may be prefabricated as a subassembly of the device shown in FIGURE 7 and may even be provided as a vaccinating device by itself, without the adhesive strip 44.

It will be seen that flap 48 and the portion of fabric strip 44 adjacent capsule 40 is arched, rather than being taut; this permits movement of flap 48 and fabric strip 44 toward the concave face of dished rigid plate member 34 during the operation of dispensing the vaccine. If the flap 48 and the fabric strip 44 were taut, then movement of flap 48 and fabric strip 44 toward dished rigid plate member 34 would be restricted.

Figure 8:
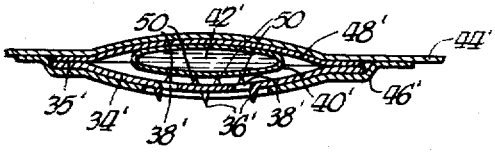
FIGURE 8 is a view similar to FIGURE 7 showing a modification of the device shown in FIGURES 6 and 7.

In the modified form shown in FIGURE 8, additional needle-like projections 50 extend inwardly from the concave side of dished member 34' and thus provide means for piercing the puncturable capsule 40' positioned between dished rigid member 34' and the fabric strip 44.

These projections 50 serve as means for opening the capsule 40' for later dispensing of the vaccine 42 through the apertures 38' in the dished rigid member 34'.

It can be seen that there has been provided a novel apparatus for standardizing vaccinations, and there has also been provided a novel vaccinating apparatus and method of vaccinating.

While there has been shown and described a particular embodiment of this invention, it will be obvious to those skilled in the art that various changes and modifications may be made therein without departing from the invention and, therefore, it is intended in the appended claims to cover all such changes and modifications as fall within the true spirit and scope of the invention.

What we claim as new, and desire to secure by Letters Patent of the United States is:

1. A device for standardizing vaccination procedures comprising a rigid member having a plurality of scarifying needles extending therefrom, an adhesive member secured to said rigid member and adapted to be secured adjacent the skin area to be scarified, whereby the scarifying needles may be substantially restricted as to relative lateral movement thereof with respect to the area to be scarified.

2. A device for standardizing vaccination procedure comprising an adhesive strip adapted to be secured to areas of skin adjacent a particular area to which the vaccine is applied and which particular area is to be scarified, and a scarifying means carried by said adhesive strip adapted to overlie said particular area, said scarifying means, as carried by said adhesive strip, being adapted to be forced against the skin to scarify said skin after said strip is properly positioned on the vaccinatee, said strip being maintained in position by said adhesive.

3. A device for standardizing vaccination procedure comprising an adhesive strip adapted to be secured to areas of skin adjacent to and on opposite sides of a particular area to which vaccine is applied and which particular area is to be scarified, and a scarifying means carried by said adhesive strip intermediate its ends adapted to overlie said particular area, said scarifying means, as carried by said adhesive strip, being adapted to be forced against the skin to scarify said skin after said strip is properly positioned on the vaccinatee, and said strip being maintained in position by the adhesive.

4. A device for standardizing vaccination procedure comprising an adhesive strip adapted to be secured to areas of skin adjacent a particular area to which the vaccine is applied and which particular area is to be scarified, and a scarifying means carried by said adhesive strip adapted to overlie said particular area, said scarifying means adapted to be forced against the skin to scarify said skin after said strip is properly positioned, said strip being maintained in position by said adhesive, and said scarifying means comprising a patch of abrasive material secured to the adhesive side of said strip.

5. A device for standardizing vaccination procedure comprising an adhesive strip adapted to be secured to areas of skin adjacent a particular area to which the vaccine is applied and which particular area is to be scarified, and a scarifying means carried by said adhesive strip adapted to overlie said particular area, said scarifying means adapted to be forced against the skin to scarify said skin after said strip is properly positioned, said strip being maintained in position by said adhesive, said scarifying means comprising a rigid plate-like member secured to the adhesive side of said strip and having a plurality of needle-like projections extending from one face of the member and positioned centrally thereon.

6. A device for standardizing vaccination procedure comprising an adhesive strip adapted to be secured to areas of skin adjacent a particular area to which the vaccine is applied and which particular area is to be scarified, and a scarifying means carried by said adhesive strip adapted to overlie said particular area, said scarifying means adapted to be forced against the skin to scarify said skin after said strip is properly positioned, said strip being maintained in position by said adhesive, said scarifying means comprising a rigid plate-like member secured to the adhesive side of said strip and having a plurality of needle-like projections extending from one face of the member and positioned centrally thereon, said needle-like projections being long enough to afford scarifying therewith and short enough to prevent laceration even if buried in the skin to their full length.

7. A device for standardizing vaccination procedure comprising an adhesive strip adapted to be secured to areas of skin adjacent a particular area to which the vaccine is applied and which particular area is to be scarified, and a scarifying means carried by said adhesive strip adapted to overlie said particular area, said scarifying means adapted to be forced against the skin to scarify said skin after said strip is properly positioned, said strip being maintained in position by said adhesive, said scarifying means comprising a rigid plate-like member secured to the adhesive side of said strip and having a plurality of needle-like projections extending from one face of the member and positioned centrally thereon, said plate-like member being of sufficient area to be engaged by substantially the entire pressing area of a thumb or finger of a person manipulating said scarifying means.

8. A device for standardizing vaccination procedure comprising an adhesive strip adapted to be secured to areas of skin adjacent a particular area to which the vaccine is applied and which particular area is to be scarified, and a scarifying means carried by said adhesive strip adapted to overlie said particular area, said scarifying means adapted to be forced against the skin to scarify said skin after said strip is properly positioned, said strip being maintained in position by said adhesive, said scarifying means comprising a rigid plate-like member secured to the adhesive side of said strip and having a plurality of needle-like projections extending from one face of the member and positioned centrally thereon, said needle-like projections being long enough to afford scarifying therewith and short enough to prevent laceration even if buried in the skin to their full-length, said plate-like member adapted to bear against the skin adjacent and surrounding the area being scarified to limit the penetration of the needle-like projections.

[9. A device for standardizing vaccination procedures comprising a scarifying means adapted to be positioned over a particular area to which vaccine has been applied and to be moved toward and away from said particular area, and a member secured to said scarifying means and having means thereon for positioning said scarifying means relative to said particular area so as to eliminate any substantial relative lateral motion between the scarifying means and the particular area being scarified, while still affording movement of said scarifying means toward and away from the particular area being scarified.]

10. A device for standardizing vaccination procedures comprising a scarifying means adapted to be positioned over a particular area to which vaccine has been applied and to be moved toward and away from said particular area, and means for positioning said scarifying means relative to said particular area so as to eliminate any substantial relative lateral motion between the scarifying means and the particular area being scarified, while still affording movement of said scarifying means toward and away from the particular area being scarified, said positioning means comprising a member secured to said scarifying means, and adhesive means on said member for securing said member in a fixed position relative to the particular skin area being scarified with said scarifying means overlying said particular area.

11. A device for standardizing vaccination procedures comprising a scarifying means adapted to be positioned over a particular area to which vaccine has been applied and to be moved toward and away from said particular area, and means for positioning said scarifying means relative to said particular area so as to eliminate any substantial relative lateral motion between the scarifying means and the particular area being scarified, while still affording movement of said scarifying means toward and away from the particular area being scarified, said positioning means comprising a flexible and relatively nonelastic member secured to said scarifying means, and adhesive means on said member for securing said member in a fixed position relative to the particular skin area being scarified with said scarifying means overlying said particular area, said flexible member affording limited movement of said scarifying means toward and away from said particular skin area being scarified.

12. A device for vaccinating people comprising a flexable adhesive strip, a member having scarifying means thereon mounted on said adhesive strip intermediate the ends of said strip, apertures in said member through which vaccine may be forced onto the skin of the person being vaccinated, and a rupturable capsule containing vaccine positioned between said member and said strip.

13. A device for vaccinating people comprising a flexible adhesive strip, a dished rigid member having scarifying means thereon mounted on said adhesive strip intermediate the ends of said strip, apertures in said dished member through which vaccine may be forced onto the skin of a person being vaccinated, said scarifying means extending from the convex side of said dished member, and a rupturable capsule containing vaccine positioned between the concave side of the dished member and the said strip.

14. A device for vaccinating people comprising a flexible adhesive strip, a dished rigid member having scarifying means thereon mounted on said adhesive strip intermediate the ends of said strip, apertures in said dished member through which vaccine may be forced onto the skin of a person being vaccinated, said scarifying means extending from the convex side of said dished member, puncturing means extending from the concave side of said dished member, and said dished member adapted to receive therein a sealed puncturable capsule containing vaccine.

15. A device for vaccinating people comprising a flexible adhesive strip, a dished rigid member having scarifying means thereon mounted on said adhesive strip intermediate the ends of said strip, apertures in said dished member through which vaccine may be forced onto the skin of a person being vaccinated, said scarifying means extending from the convex side of said dished member, a rupturable capsule containing vaccine positioned between the concave side of the dished member and said strip, and a flexible sterile flap interposed between said capsule and said adhesive strip, operative to retard permeation of liquid vaccine released from said capsule through said strip.

16. A device for vaccinating people comprising a dished rigid member having a flange extending from the edge thereof, scarifying means extending from the convex side of said dished member, apertures in said dished member through which vaccine may be forced onto the skin of a person being vaccinated, a rupturable capsule containing vaccine positioned adjacent the concave side of the dished member, and a flexible member covering the capsule within said dished member and being movable toward the concave side of said dished member, whereby the capsule may be ruptured and the vaccine may be forced through said apertures.

*17. A combination biological-dispensing and scarifying device which may be maintained sterile by individual packaging in a sterile package and which is to be discarded after a single use thereof, said combination device comprising: a multiple-point scarifying instrument adapted to be selectively positioned over a particular skin area of a person and to be moved by only digital manipulation toward and away from said particular skin area to effect multiple pressure-puncture scarifications to limited depth in said person's skin, control means secured to said scarifying instrument and providing means thereon adapted to permit of selective manual positioning of said scarifying instrument relative to said particular area and to eliminate any substantial relative lateral motion between the scarifying instrument and said particular area to be scarified, while still affording puncturing movement of said scarifying instrument under only digital manipulation toward and away from the particular area being scarified, and a selected specimen of biological substance pre-assembled upon and carried by said scarifying instrument for dispensing application to said particular area from the exterior surfaces of a plurality of the points of said scarifying instrument, said combination device affording use thereof as desired, including at times long subsequent to the time of pre-assembly.*

*18. A combination biological-dispensing and scarifying device which may be maintained sterile by individual packaging in a sterile package and which is to be discarded after a single use thereof, said combination device comprising: a generally planar instrument defining a support member having integral therewith a plurality of solid scarifying points of the same material as said support member extending transversely therefrom in one general direction from one side of said support member and adapted for scarifying by pressure only and to a limited depth a selected small skin area of a person with only substantially simultaneous pressure punctures of the skin by substantially all of said plurality of scarifying points, and a selected specimen of biological substance pre-assembled upon and carried by said instrument and arranged for dispensing application to said selected skin area from the exterior surfaces of said scarifying points, said combination device affording use thereof as desired, including at times long subsequent to the time of pre-assembly.*

References Cited in the file of this patent or the original patent

UNITED STATES PATENTS

| | | |
|---|---|---|
| 652,999 | Denis | July 3, 1900 |
| 1,212,927 | Flood | Jan. 16, 1917 |
| 2,235,436 | Laub | Mar. 18, 1941 |
| 2,489,675 | Roberts | Nov. 29, 1949 |
| 2,522,309 | Simon | Sept. 12, 1950 |
| 2,575,648 | Willson | Nov. 20, 1951 |
| 2,619,962 | Rosenthal | Dec. 2, 1952 |

FOREIGN PATENTS

| | | |
|---|---|---|
| 43,081 | Germany | Aug. 23, 1888 |